United States Patent [19]
Buzzetti et al.

[11] Patent Number: 5,457,097
[45] Date of Patent: Oct. 10, 1995

[54] ANDROST-4-ENO[4,5-B]PYRROLE DERIVATIVES

[75] Inventors: Franco Buzzetti, Monza; Antonio Longo; Enrico Di Salle, both of Milano, all of Italy

[73] Assignee: Farmitalia Carlo Erba S.r.l., Milano, Italy

[21] Appl. No.: 92,789

[22] Filed: Jul. 19, 1993

[30] Foreign Application Priority Data

Aug. 11, 1992 [GB] United Kingdom .................. 9217035

[51] Int. Cl.$^6$ .............................. C07J 1/00; A61K 31/56
[52] U.S. Cl. ................ 514/176; 540/49; 540/58
[58] Field of Search .................... 540/58, 49, 55, 540/56; 514/176

[56] References Cited

U.S. PATENT DOCUMENTS

| | | | |
|---|---|---|---|
| 3,032,551 | 5/1962 | Orr et al. | 540/58 |
| 3,282,928 | 11/1966 | Cantrall et al. | 260/239.5 |
| 4,757,061 | 7/1988 | Faustini et al. | |
| 4,822,528 | 4/1989 | Columbo et al. | |
| 4,824,830 | 4/1989 | Buzzetti et al. | |
| 4,873,233 | 10/1989 | Villa et al. | |

FOREIGN PATENT DOCUMENTS

| | | |
|---|---|---|
| 0260975 | 3/1988 | European Pat. Off. |
| 2171100 | 8/1986 | United Kingdom |

OTHER PUBLICATIONS

*Biochemical Pharmacology*, vol. 34, pp. 3213–3219 (1985).
*Drugs of the Future*, vol. 17, pp. 278–280 (1992).
*Drugs of the Future*, vol. 18, pp. 599–600 (1993).
*Therapeutic Patents*, Jun. 1993.
*Chemical & Pharmaceutical Bulletin*, vol. 17, No. 12, Dec. 1969, pp. 2586–2598, Taichiro Komeno, et al., "Thiosteroids. XXII. The Intramolecular Cyclization of 6–Acylthio–, Acyloxy–, and Acylamino–4–En–3–One Steroids. Pentacyclic Steroids".

*Primary Examiner*—Nicholas Rizzo
*Attorney, Agent, or Firm*—Oblon, Spivak, McClelland, Maier & Neustadt

[57] ABSTRACT

This invention refers to compounds of formula (I)

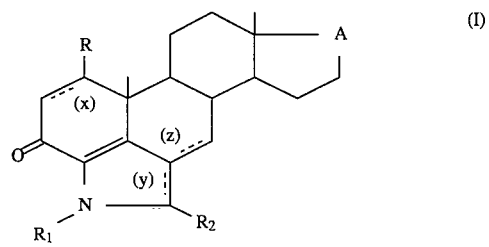

wherein x, y, z represent single or double bonds;

R is hydrogen or $C_1$–$C_4$ alkyl;

$R_1$ is hydrogen or an acyl group;

$R_2$ is hydrogen; $C_1$–$C_4$ alkyl unsubstituted or substituted by phenyl; phenyl unsubstituted or substituted by $C_1$–$C_4$ alkyl or $C_1$–$C_4$ alkoxy; and A is a >C=O, >C $\sim$ OH or >C $\sim$ OR$_3$ group, in which $R_3$ is an acyl group provided that one of z and y is a double bond and the other is a single bond.

The compounds are useful as aromatase inhibitors.

9 Claims, No Drawings

ANDROST-4-ENO[4,5-B]PYRROLE DERIVATIVES

The present invention relates to new androst-4-eno [4,5-b]pyrroles, to a process for their preparation, to pharmaceutical compositions containing them, and to their use as therapeutic agents, in particular in the treatment of hormone-dependent diseases in mammals.

Basic and clinical data indicate that aromatized metabolites off androgens, i.e. the estrogens, are the hormones involved in the pathogenic cellular changes associated with the growth of some hormone-dependent cancers, such as breast, endometrial and ovarian carcinomas.

Estrogens are also involved in the pathogenesis of benign prostatic hyperplasia.

Endogenous estrogens are ultimately formed from either androstenedione or testosterone as immediate precursors. The reaction of central importance is the aromatization of the steroidic ring A, which is performed by the enzyme aromatase. As aromatization is a unique reaction and the last in the series of steps in the biosynthesis of estrogens, it has been envisaged that an effective inhibition of the aromatase, resulting from compounds able to interact with the aromatizing steps, may have useful application for controlling the amount of circulating estrogens, estrogen-dependent processes in reproduction, and estrogen-dependent tumors.

Known steroidal substances which have been reported to be endowed with an aromatase-inhibiting action are, for example, $\Delta^1$-testololactone (U.S. Pat. No. 2,744,120), 4-hydroxyandrost- 4-ene-3,17-dione and esters thereof (see, for example, U.S. Pat. No. 4,235,893), 10-(1,2-propadienyl)-estr- 4-ene-3,17-dione (U.S. Pat. No. 4,289,762), 10-(2-propynyl)-estr- 4-ene-3,17-dione (J.Amer.Chem.Soc., 103, 3221 (1981) and U.S. Pat. No. 4,322,416), 19-thioandrostene derivatives (Europ.Pat.Appl. 100,566), androsta-4,6-diene-3,17-dione, androsta-1,4,6-triene-3,17-dione (G.B.Pat.Appl. 2,100,601A), androsta-1,4-diene-3,17-dione (Cancer Res. (Suppl.) 42, 3327 (1982)), 6-alkenylenandrosta- 1,4-diene-3,17-diones (U.S. Pat. No. 4,808,816 and U.S. Pat. No. 4,904,650) and 6-alkenylenandrosta-1,4-dien-17-ol-3-one derivatives (U.S. Pat. No. 4,873,233).

The present invention provides new compounds having the Following general Formula (I)

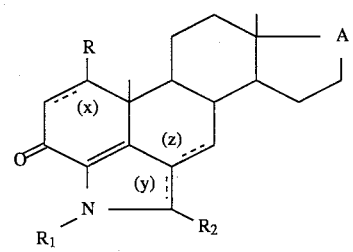

(I)

wherein x, y and z represent single or double bonds;

R is hydrogen or $C_1$–$C_4$ alkyl;

$R_1$ is hydrogen or an acyl group;

$R_2$ is hydrogen; $C_1$–$C_4$ alkyl unsubstituted or substituted by phenyl, or phenyl unsubstituted or substituted by $C_1$–$C_4$ alkyl or $C_1$–$C_4$ alkoxy;

A is a >C=O, >C ⌇OH or >C ⌇$OR_3$ group, in which $R_3$ is an acyl group provided that one of z and y is a double bond and the other is a single bond.

Compounds falling within the scope of formula (I) above are all the possible isomers, stereoisomers and their mixtures, and the metabolites and the metabolic precursors or bioprecursors of the compound of formula (I). In the formulae of specification the heavy solid lines ▰▰▰ indicate that a substituent is in the β-configuration, i.e. above the plane of the ring, whereas a dotted line ( - - - ) indicates that a substituent is in the α-configuration, i.e. beneath the plane of the ring, and a wavy line ⌇⌇ indicates that a substituent may be either in the α-configuration, or in the β-configuration or in both, i.e. a mixture thereof. In particular when in the compounds of formula (I) A is C ⌇OH or >C ⌇$OR_3$ substituent may be either in the α- or in the β-configuration or in both, i.e. a mixture thereof. Analogously, when x or y is a single bond, the R or $R^2$ substituent, respectively, may be either in the α- or β-configuration or in both, i.e. a mixture thereof. Accordingly, object of the present invention are also all the possible isomers, e.g. the single 1α, 17α; 1α, 17β; 1β, 17α and 1β, 17β epimers, as well as all possible mixtures thereof, e.g. 1(α,β), 17α; 1(α,β), 17β; 1α,1 7(α,β); 1β, 17(α,β) and 1(α,β), 17(α,β)-isomers of the compounds of formula (I). Hence a compound of the invention herein specifically mentioned, without any indication of its stereochemistry, is intended to represent all the possible single isomers or mixtures thereof.

In this specification the alkyl groups and the alkyl moiety in the alkoxy or acyl group may be a straight or branched chain.

A $C_1$–$C_4$ alkyl group is preferably a methyl or ethyl group, more preferably a methyl group.

An acyl group may be a residue of any physiologically tolerable acid. Preferred examples of said acids are the $C_1$–$C_4$ alkanoic ones; in particular acetic, propionic and butyric acids.

When $R_2$ is a $C_1$–$C_4$ alkyl group substituted by phenyl $R_2$ is preferably benzyl.

When $R_2$ is a phenyl substituted by a $C_1$–$C_4$ alkyl or $C_1$–$C_4$ alkoxy $R_2$ is preferably para-methylphenyl or paramethoxyphenyl.

As stated above, the present invention also includes within its scope pharmaceutically acceptable bio-precursors (otherwise known as pro-drugs) of the compounds of formula (I), i.e. compounds which have a different formula to formula (I) above but which nevertheless upon administration to a human being are converted directly or indirectly in vivo into a compound of formula (I).

Preferred compounds of the invention are the compounds of formula (I) wherein

A is a >C=O,>C ⌇OH or >C ⌇OAc

R, $R_I$ and $R_2$ are hydrogen;

x, y, z are single or double bonds;

provided that one of y and z is a double bond and the other is a single bond.

Examples of specific compounds of the invention are the following compounds:

3,17-dioxo-1'H-androst-4-eno[4,5-b]pyrrole;

17β-hydroxy-3-oxo-1'H-androst-4-eno[4,5-b]pyrrole;

17β-acetoxy-3-oxo-1'H-androst-4-eno[4,5-b]pyrrole;

3,17-dioxo-1'H-androsta-1,4-dieno[4,5-b]pyrrole;

17β-hydroxy-3-oxo-1'H-androsta-1,4-dieno[4,5-b]pyrrole;

17β-acetoxy-3-oxo-1'H-androsta-1,4-dieno[4,5-b]pyrrole.

3,17-dioxo-1'H-androsta-4,6-dieno [4,5-b]pyrroline;

17β-hydroxy-3-oxo-1'H-androsta-4,6dieno[4,5-b]pyrroline;

17β-acetoxy-3-oxo-1'H-androsta-4,6-dieno[4,5-b]pyrroline;

3,17-dioxo-1'H-androsta-1,4,6-trieno[4,5-b]pyrroline;

17β-hydroxy-3-oxo-1'H-androsta-1,4,6-trieno[4,5-b]pyrroline; and

17β-acetoxy-3-oxo-1'H-androsta-1,4,6-trieno[4,5-b]pyrroline, as well as, where appropriate, the α, β mixtures of the above reported 17α,17β epimers.

The compounds of the invention can be obtained by a process comprising:

a) reacting a compound of formula (II)

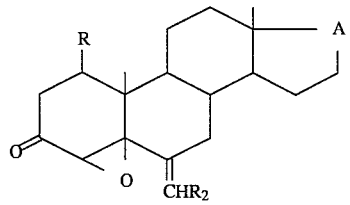

wherein R, $R_2$ and A are as defined above, with a compound of formula (III)

$$M-N_3 \quad (III)$$

wherein M is an alkali metal or ammonium cation or a tri-$C_1$–$C_6$-alkylsilyl group, so obtaining a compound of formula (I), wherein x and z are single bonds, y is double bond, R, R2 and A are as defined above and $R_1$ is hydrogen; or b) pyrolysing a compound of formula (IV)

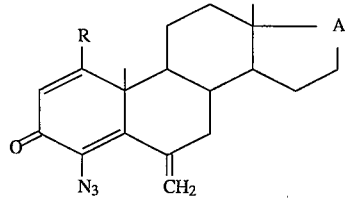

wherein R and A are as defined above, thus obtaining a compound of formula (I), wherein x and y are double bonds, z is single bond, $R_1$ and $R_2$ are hydrogen, and R and A are as defined above; or, if desired, c) deacylating a compound of formula (V)

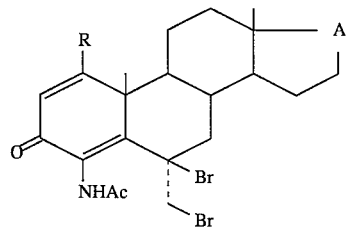

wherein A and R are as defined above, so obtaining a compound of formula (I) wherein x and z are double bonds, y is single bond, $R_1$ and $R_2$ are hydrogen, A and R are as defined above; and/or, if desired, d) dehydrogenating a compound of formula (IA)

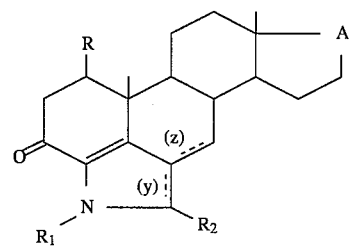

wherein y, z, R, $R_1$, $R_2$ and A are as defined above so obtaining a compound of formula (I), wherein x is double bond and y, z, R, $R_1$, $R_2$ and A are as defined above; and/or if desired e) reducing selectively a compound of formula (IB)

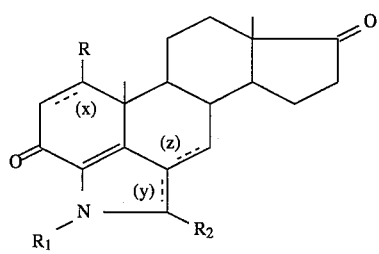

wherein x, y, z, R, $R_1$ and $R_2$ are as defined above, thus obtaining a compound of formula (I) wherein A is >C ⋯OH, x, y, z, R, $R_1$ and R2 are as defined above; and/or, if desired, f) acylating selectively a compound of formula (IC)

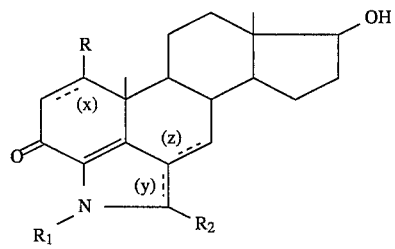

wherein x, y, z, R, $R_1$ and $R_2$ are as defined above, thus obtaining a compound of formula (I) wherein x, y, z, R, $R_1$, and $R_2$ are as defined above and A is a >C ⋯$OR_3$ group in which $R_3$ is an acyl group; and/or if desired, g) acylating a compound of formula (ID)

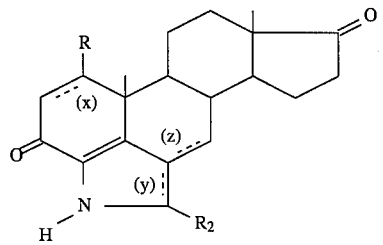

wherein x, y, z, R and $R_2$ are as defined above thus obtaining a compound of formula (I) wherein x, y, z, R and $R_2$ are as defined above, $R_1$ is an acyl group and A is a carbonyl group; and, if desired, converting a compound of formula (I) into another compound of formula (I), and/or, if desired, separating a mixture of isomers of compounds of formula (I) into the single isomers.

* * * * *

The reaction between a compound of formula (II) and a compound of formula (III) according to the process step a), is preferably carried out in an organic solvent such as, for instance, N,N-dimethylformamide, N,N-dimethylacetamide or dimethylsulfoxide; some Water or an aqueous alcoholic, e.g. methanolic or ethanolic solution may be added, if desired to increase the solubility of the azide of formula (III). The reaction is performed at temperatures ranging from about 90° C. to about 150° C. and applying reaction times from ½ hour to several hours, for example 5 hours. Preferred compounds of formula (III) are sodium azide, lithium azide, ammonium azide, trimethylsilylazide and dimethyl-tert-butylsilylazide. The pyrolysis of a compound of formula (IV) according to the process step (b), may be performed according to known methods, e.g. by heating a solution of the compound in an inert solvent such as DMSO for several hours at temperatures ranging from about 50° C. to about 150° C. The deacylation of a compound of Formula (V) according to process step (c), may be performed according to known methods, e.g. by treatment with hydrochloric acid in alcoholic solution at temperatures ranging from 0° C. to reflux temperature.

* * * * *

The dehydrogenation of a compound of Formula (IA) according to the process step (d), may be performed according to known methods, e.g. by treatment with DDQ according to D. Walker and J. D. Hiebert in Chem. Rev. 67 156 (1967), or by treatment with selenium dioxide, chloranil or benzeneseleninic anhydride. Preferably such reaction is performed by treatment with DDQ. Preferably also an inert solvent such as dioxane, benzene, toluene or dichloromethane, a temperature ranging from about 40° C. to about 100° C. and reaction time lasting from about 1 hour to about 24 hours are employed.

* * * * *

The selective reduction of a compound of formula (IB), according to the process step (e), may be carried out by well known methods, for example as described by C. Djerassi in Steroid Reactions (1963) or by D. Fried in Organic Reactions in Steroid Chemistry Vol. I (1972). Preferably the reduction is carried out with complexed metal hydrides, in particular with sodium borohydride in an inert organic solvent in particular in methanol solution at temperatures ranging from about 0° C. to about 50° C.

* * * * *

The acylation of a compound of formula (IC) according to the process step (f) can be performed by reaction with a reactive derivative of a suitable carboxylic acid, such as an anhydride or halide, in the presence of a basic agent, at temperatures ranging from about 0° to about 50° C. Preferably the acylation is carried out by reaction with the respective anhydride in the presence of an organic base, such as pyridine.

* * * * *

The acylation of a compound of formula (ID) according to the process step (g) can be performed, e.g. by reaction with a suitable carboxylic anhydride in the presence of a basic agent at temperatures ranging from room temperature to reflux temperature. Preferably the acylation is carried out with carboxylic anhydride at reflux temperatures in the presence of sodium acetate base as described by W. A. Remers et al. in J. Org. Chem., 36, 1232 (1971).

* * * * *

The separation of a mixture of isomers into the single isomers as well as the conversion of a compound of formula (I) into another compound of formula (I) may be carried out according to known methods.

* * * * *

The conversion of a compound of formula (I) into another compound of formula (I) includes for example the conversion of a 17β-hydroxy derivative of a compound of formula (I) into the corresponding 17α-hydroxy derivative which may be carried out by basic catalysis, e.g. with 0.1N sodium hydroxide in an aliphatic alcohol, e.g. ethanol.

Other examples of conversions of a compound of formula (I) into another compound of formula (I) are:

the dehydrogenation of a compound of formula (I) wherein x is single bond and y, z, R, $R_1$, $R_2$ and A are as defined above, into a corresponding compound of formula (I) wherein x is a double bond, which reaction may be carried out by the method reported above for the process step (d);

the reduction of a compound of Formula (I) wherein x, y z, R, $R_1$, $R_2$ are as defined above and A is a >C=O group to a corresponding compound of formula (I) wherein A is a >CH—OH group, which reaction may be carried out by the method reported above for the process step (e);

the acylation of a compound of formula (I) wherein R, $R_1$, $R_2$, z, y and z are as defined above and A is C ⋯ OH to a corresponding compound of formula (I) wherein A is >C ⋯ $OR_3$ group wherein $R_3$ is an acyl group, the reaction may be carried out by the method reported above for the process step (f).

The acylation of a compound of formula (I) wherein x, y, z, R and $R_2$ are as defined above, A is a >=O group and is hydrogen, to a corresponding compound of formula (I) wherein x, y, z, R and $R_2$ are as defined above A is a >=O group and $R_1$ is an acyl group, which reaction may be carried out by the method reported above for the process step (g).

A compound of formula (II) can be obtained by epoxidizing a compound of formula (VI)

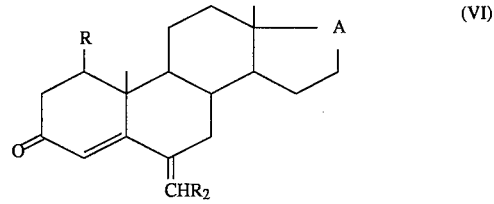

wherein A, R and $R_2$ are as defined above.

The oxidation may be carried out by treatment with a suitable oxidizing agent, e.g. with 36% $H_2O_2$ in alcoholic alkali hydroxide solution, preferably KOH or NaOH in methanol, at a temperature ranging from about 0° to about 30° C. for reaction times lasting from 2 hours to several days.

A compound of formula (VI) may be in its turn obtained by alkylidenation of a compound of formula (VII)

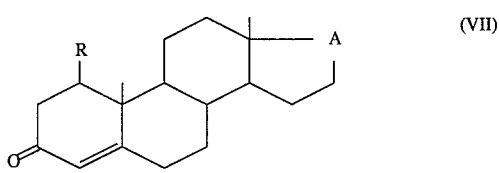

wherein R and A are as defined above, according to known methods, e.g. according to the method of K. Annen (Synthesis 1982, 34). Preferably a compound of formula (VII) is reacted with unsubstituted or appropriately $R_2$ substituted formaldehyde diethylacetal [$CH_2(OEt)_2$ or $R_2CH(OEt)_2$], wherein $R_2$ is as defined above, in refluxing chloroform, in the presence of catalytic amounts of phosphoryl chloride and sodium acetate.

Alternatively a compound of formula (VI) wherein A is a C ⋯ $OR_3$ group may be obtained from a compound of formula (VIII),

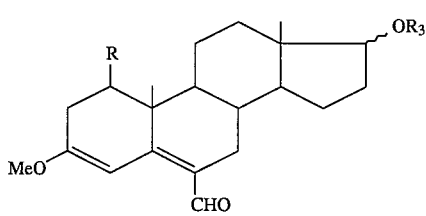

wherein R and $R_3$ are as defined above by Grignard reaction with a Grignard reagent of formula $R_2$ MgBr and subsequent hydrolysis of enolether group with aqueous mineral acid. The Grignard reaction may be carried out according to reaction conditions well known in organic chemistry, e.g. as described by M. S. Karasch and O Reinmuth in "Grignard reactions of non metallic substances".

The compounds of formula (VII) and (VIII), are known compounds or may be obtained by known methods from known compounds.

A compound of formula (IV) can be obtained from a compound of formula (IX)

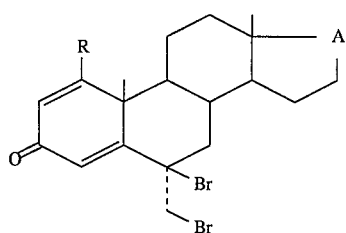

wherein R and A are as defined above by reaction with a compound of formula (III), preferably with sodium azide. Preferably the reaction is carried out in an organic solvent, such as dimethylformamide, dimethylacetamide or dimethylsulfoxide in the presence of an inorganic base such as lithium carbonate by applying reaction temperatures ranging from about 50° C. to about 100° C.

A compound of formula (IX) may be obtained by bromuration of a compound of formula (X)

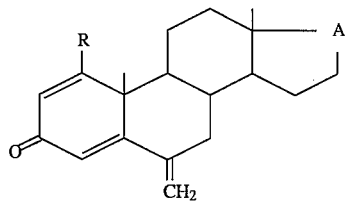

wherein R and A are as defined above.

Preferably the bromuration is carried out in an inert organic solvent such as acetic acid, ether or mixtures thereof at temperatures ranging from about −20° C. to room temperature. Preferably exactly 1 mol eq. of bromine is used.

The compounds of formula (X) are known compounds (see U.S. Pat. No. 4,822,528) or may be obtained by known methods from known compounds.

A compounds of formula (V) may be obtained by bromuration of a compound of formula (XI)

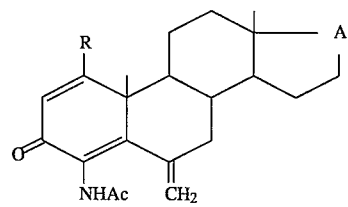

wherein R and A are as defined above,. Preferably the bromuration is carried out in an inert organic solvent such as acetic acid, ether or mixtures thereof at temperatures ranging from about −20° C. to about room temperature and by applying exactly 1 molequivalent of bromine.

A compound of formula (XI) may be obtained from a compound of formula (IV) by reduction to an amino intermediate and successive acetylation. The reduction of the azido group may be performed e.g. with triphenylphosphine in THF solution or with sodium sulfide in aqueous acetone solution. The successive acetylation may be carried out with acetanhydride or acetyl chloride according to the method used in process step (f).

When in the new compounds of the present invention and in the intermediate products thereof groups are present, which need to be protected before submitting them to the here-above illustrated reactions, they may be protected before the reactions take place and then deprotected at the end of the reactions, according to well known methods in organic chemistry.

The compounds of the present invention are inhibitors of the biotransformation of androgens into estrogens, i.e., they are steroidal aromatase inhibitors.

The aromatase inhibitory activity of these compounds was demonstrated by employing the in vitro test described by Thompson and Siiteri (E. A. Thompson and P. K. Siiteri, J. Biol. Chem. 249, 5364 (1974) which utilizes the human placental microsomal fraction as enzyme source. In this test the aromatization rate of androstenedione into estrone was evaluated by incubating [1β-$^3$H] androstenedione (50 nM) in the presence of NADPH with the enzyme preparation and by measuring the amount of $^3H_2O$ formed during 15 min incubation at 37° C.

The concentration of each compound required to reduce control aromatase activity by 50% ($IC_{50}$) was determined by plotting % inhibition versus log of inhibitor concentration.

Thus, for example in the above test, a representative compound of the invention, namely 3,17-dioxo-1'H-androsta- 1,4-dieno[4,5-b]pyrrole was found to produce 50% inhibition off human placental aromatase at the concentration of 120 nM.

In view of the above indicated ability to inhibit aromatase and, consequently, to reduce estrogen levels, the compounds of the invention are useful in mammals, including humans, in the treatment and prevention of various estrogen-dependent diseases, i.e. breast, endometrial, ovarian and pancreatic cancers, gynecomastia, benign breast disease, endometriosis, polycystic ovarian disease and precocious puberty. Another application of the compounds of the invention is in the therapeutic and/or prophylactic treatment of prostatic hyperplasia, a disease of the estrogen-dependent stromal tissue.

The compounds of the invention can find also use for the treatment of male infertility associated with oligospermia and for female fertility control, by virtue of their ability to inhibit ovulation and egg nidation.

In view of their low toxicity the compounds of the invention can be used safely in medicine. For example, the approximate acute toxicity (LD$_{50}$) of the compounds of the invention in the mouse, determined by single administration of increasing doses and measured on the seventh day after the treatment was found to be negligible.

The compounds of the invention can be administered in a variety of dosage forms, e.g. orally, in the form of tablets, capsules, sugar or film coated tablets, liquid solutions or suspensions; rectally, in the form of suppositories, parenterally, e.g. intramuscularly, or by intravenous injection or infusion.

The dosage depends on the age, weight, conditions of the patient and administration route; for example, the dosage adopted For oral administration to adult humans may range form about 10 to about 150–200 mg pro dose, from 1 to 5 times daily.

The invention includes pharmaceutical compositions comprising a compound of the invention in association with a pharmaceutically acceptable excipient (which can be a carrier or diluent).

The pharmaceutical compositions containing the compounds of the invention are usually prepared following conventional methods and are administered in a pharmaceutically suitable form.

For example the solid oral forms may contain, together with the active compound, diluents, e.g. lactose, dextrose, saccharose, cellulose, corn starch or potato starch; lubricants, e.g. silica, talc, stearic acid, magnesium or calcium stearate, and/or polyethylene glycols; binding agents, e.g. starches, arabic gums, gelatin, methylcellulose, carboxymethylcellulose or polyvinyl pyrrolidone; disaggregating agents, e.g. a starch, alginic acid, alginates or sodium starch glycolate; effervescing mixtures; dyestuffs, sweeteners; wetting agents, such as lecithin, polysorbates, laurylsulphates; and, in general, non-toxic and pharmacologically inactive substances used in pharmaceutical formulations. Said pharmaceutical preparations may be manufactured in known manner, for example, by means of mixing, granulating, tabletting, sugar-coating, or film-coating processes. The liquid dispersion for oral administration may be e.g. syrups, emulsions and suspensions.

The syrups may contain as carrier, for example, saccharose or saccharose with glycerine and/or mannitol and/or sorbitol.

The suspensions and the emulsions may contain as carrier, for example, a natural gum, agar, sodium alginate, pectin, methylcellulose, carboxymethylcellulose, or polyvinyl alcohol.

The suspensions or solutions for intramuscular injections may contain, together with the active compound, a pharmaceutically acceptable carrier, e.g. sterile water, olive oil, ethyl oleate, glycols, e.g. propylene glycol, and if desired, a suitable amount of lidocaine hydrochloride. The solutions for intravenous injections or infusions may contain as carrier, for example, sterile water or preferably they may be in the form of sterile, aqueous, isotonic saline solutions.

The suppositories may contain together with the active compound a pharmaceutically acceptable carrier, e.g. cocoabutter, polyethylene glycol, a polyoxyethylene sorbitan fatty acid ester surfactant or lecithin.

The following examples illustrate but do not limit the invention:

EXAMPLE 1

3,17-dioxo-1'H-androst-4-eno[4,5-b]pyrrole

To a stirred solution of 4,5-epoxy-6-methylen-androstan-3,17-dione (3,14 g, 10 mmol) in dimethyl sulphoxide (110 ml) and conc. sulphuric acid (1,5 ml) were added powdered sodium azide (28,60 g, 440 mmol). The resulting mixture was heated at 100° C. external temperature and maintained at this temperature for another ½ hour. Then the reaction mixture was cooled, poured onto iced water and extracted with ethyl acetate 3 times. The combined extracts were washed with saturated sodium chloride solution, dried over sodium sulfate and evaporated in vacuum to yield a residue which is purified by flash column chromatography on silica gel. Elution with hexane-ethylacetate 1:1 gave the title compound in 50% yield (1550 mg).

$C_{20}H_{25}NO_2$ calcd: C 77.13 H 8.09 N 4,50 found: C 77.05 H 8.01 N 4,35 MS (m/z) 311. IR (KBr) cm$^{-1}$: 3340 (NH), 3220 (NH), 1730 (CO), 1625 (CO, C=C)

By proceeding analogously the following compounds can be prepared:

17β-acetoxy-3-oxo-1'H-androst-4-eno[4,5-b]pyrrole; and

17β-hydroxy-3-oxo-1'H-androst-4-eno[4,5-b]pyrrole.

EXAMPLE 2

3,17-dioxo-1'H-androsta-1,4-dieno[4,5-b]pyrrole

A solution of 3,17-dioxo-1'H-androst-4-eno[4,5-b]pyrrole (3.11 g, 10 mmol) and benzene seleninic anhydride (3,60 g, 10 mmol) in chlorobenzene (300 ml) was heated for 1 hour at 90°–100 C.

Then the solvent was removed in vacuo and the residue chromatographed on silica gel using hexane/ethylacetate 1:1 as elegant to give pure title compound in about 55% yield (1700 mg).

$C_{20}H_{23}NO_2$ calcd: C 77.69 H 7.49 N 4.53 found: C 77.55 H 7.35 N 4.45 MS (m/z): 309. IR cm$^{-1}$(KBr): 3430, 3210 (NH), 1735 (17-keto), 1630 (3-keto), 1605 (C=C).

By proceeding analogously the following compounds can be prepared:

17β-acetoxy-3-oxo-1'H-androsta-1,4-dieno[4,5-b]pyrrole; and

17β-hydroxy-3-oxo-1'H-androsta-1,4-dieno[4,5-b]pyrrole.

EXAMPLE 3

17β-hydroxy-3-oxo-1'H-androst-4-eno[4,5-b]pyrrole

To a stirred solution of 3,17-dioxo-1'H-androst-4eno[4,5-b]pyrrole (3,11 g, 10 mmol) in methanol (200 ml) was added sodium borohydride (570 mg, 15 mmol) over a period of 20 min at 0° C. and stirring was continued for 1 hour at 0° C. After addition of few drops of acetic acid, the mixture was concentrated under vacuum, diluted with water and then extracted with ethyl acetate. The combined organic phases were washed with saline solution, dried over sodium sulfate and then evaporated in vacuum.

The residue was submitted to column chromatography on silica gel. Gradient elution with hexane/ethylacetate mixtures afforded pure title compound (1880 mg, 60% yield).

$C_{20}H_{27}NO_2$ calcd: C 76.64 H 8.68 N 4.47 found : C 76.55 H 8.54 N 4.35 MS (m/z) 313. IR cm$^{-1}$ (KBr): 3400-3200 (NH, OH), 1630 (CO, C=C)

According to the above described procedure and starting from the appropriate compound of formula (I) respectively one can prepare the following products:

17β-hydroxy-3-oxo-1'H-androsta-1,4-dieno[4,5-b]pyrrole;

17β-hydroxy-3-oxo-1'H-androsta-4,6-dieno[4,5-b]pyrroline; and

17β-hydroxy-3-oxo-1'H-androsta-1,4,6-trieno[4,5-b]pyrroline.

EXAMPLE 4

17β-acetoxy-3-oxo-1'H-androst-4-eno[4,5-b]pyrrole

To a cooled solution of 17β-hydroxy-3-oxo-1'H-androst-4eno[4,5-b]pyrrole (3,13 g, 10 mmol) in dry pyridine (5 ml) was added acetic anhydride (4,084 g, 40 mmol) and the mixture maintained at 0°–5° C. overnight. The solvent was removed in vacuum, the residue dissolved in dichloromethane, the organic layer washed with water and then evaporated under reduced pressure. The crude product was crystallized from benzene to yield pure title compound in 80% yield (2.84 g).

$C_{20}H_{29}NO_3$ calcd: C 74.33 H 8.22 N 3.94 found: C 74.25 H 8.15 N 3.85 MS (m/z) 355. IR $cm^{-1}$ (KBr): 3420, 3200 (NH), 1740 ($OCOCH_3$), 1630 (CO, C=C).

By proceeding analogously the following compounds can be prepared:

17β-acetoxy-3-oxo-1'H-androsta-4,6-dieno[4,5-b]pyrroline;and

17β-acetoxy-3-oxo-1'H-androsta-1,4,6-trieno[4,5-b]pyrroline.

EXAMPLE 5

N-acetyl-3-oxo-1'H-androst-4-eno[4,5-b]pyrrole

A mixture of 3,17-dioxo-1'H-androst-4-eno[4, 5-b]pyrrole (3.11 g, 10 mmol), potassium acetate (0,980 g, 10 mmol) and acetic anhydride (10 ml) was heated at reflux temperature for 16 hours and then concentrated under vacuum. This extract was filtered and concentrated on a steam bath as hexane was added. When the first crystals appeared, the mixture was cooled and after a while the crystals were filtered. Recrystallization from acetone-hexane gave pure title compound in 70% yield (2.47 g)

$C_{22}H_{25}NO_3$ calcd: C 74.76 H 7.70 N 3.96 found: C 74.55 H 7.65 N 3.85 MS (m/z) 353. IR $cm^{31}$ (KBr): 1740 (CO, 1730 (–CON<), 1625 (CO, C=C).

According to the above described procedure and starting from the appropriate compound of formula (I) one can prepare the following product:

N-acetyl-3-oxo-1'H-androsta-1,4-dieno[4,5-b]pyrrole.

EXAMPLE 6

3,17-dioxo-1'H-androsta-1,4-dieno[4,5-b]pyrrole

A solution of 4-azido-6-methylenandrosta-1,4-diene-3, 17-dione (3.374 g, 10 mmol) in dimethylsulfoxide (150 ml) was heated for 2 h at about 90° C. under nitrogen. The reaction mixture was cooled, the raw product precipitated by water addition and then purified by flash chromatography on silica gel using hexane/ethyl acetate 1:1 as eluant. Thus pure title compound was obtained in about 30% yield.

$C_{20}H_{23}NO_2$ calcd: C 77.69 H 7.49 N 4.53 found C 77.61'H 7.41 N 4.35 MS m/z 309 IR $cm^{-1}$ (KBr): 3430, 3210 (NH), 1735 (17-keto), 1630 (3-keto), 1605 (C=C).

EXAMPLE 7

3,17-dioxo-1'H-androsta-1,4,6-trieno[4,5-b]pyrroline

A solution of 4-acetamino-6-bromo-6-bromomethylandrosta-1,4-diene-3,17-dione (513,3 mg, 1 mmol) in a mixture of ethanol (20 ml) and 36% hydrochloric acid (2 ml) was heated for 3 h at reflux. The solution was made alkaline with 40% NaOH, concentrated under vacuum and then extracted 2× with ethyl acetate. The organic phase was dried ($Na_2SO_4$), evaporated to dryness under vacuum and the residue chromatographed on silica gel. Gradient elution with hexane/ethyl acetate mixture afforded pure title compound in about 35% yield.

$C_{20}H_{23}NO_2$ calcd: C 77.64 H 7.49 N 4.53 found : C 77.49 H 7.40 N 4.35 MS (m/z) 309 IR $cm^{-1}$ (KBr): 3400, 3200 (NH), 1735 (17-keto), 1640 (3-Keto), 1600 (C=C)

By proceeding analogously the following compounds can be prepared:

17β-acetoxy-3-oxo-1'H-androsta-1,4,6-trieno [4,5-b]pyrroline;

17β-hydroxy-3-oxo-1'H-androsta-1,4,6-trieno [4,5-b]pyrroline;

3,17-dioxo-1'H-androsta-4,6-dieno [4,5-b]pyrroline;

17β-acetoxy-3-oxo-1'H-androst-4,6-dieno [4,5-b]pyrroline; and

17β-hydroxy-3-oxo-1'H-androst-4,6-dieno [4,5-b]pyrroline.

EXAMPLE 8

4,5-epoxy-6-methylenandrosta-3,17-dione

A mixture of sodium acetate (1 g), anhydrous chloroform (30 ml), formaldehyde diethyl acetal (30 ml, 0.24 mol), phosphoryl chloride (3.8 ml, 0.04 mol), and androst-4-ene-3,17-dione (0.78 g, 2.7 mmol) was stirred at reflux for about 7 hours, i.e. until the starting material had disappeared. The suspension was allowed to cool and under vigorous stirring a saturated sodium carbonate solution was added dropwise until the pH of the aqueous layer became alkaline. The organic layer was separated, neutralized with water washings, and dried with sodium sulfate. After concentration under reduced pressure the oily residue was purified by chromatography on silica gel using hexane/ethylacetate as eluant. Thus almost pure 6-methylenandrost- 4-ene-3,17-dione was obtained in 60% yield (0.843 g).

6-methylenandrost-ene-3,17-dione (0.843 g, 2.8 mmol) was dissolved in methanol (35 ml) and the solution cooled to 0° C. Thereupon ice cold 36% $H_2O_2$ (3 ml) and 2% NaOH (1.5 ml) was added. The mixture was stirred for 1 h, allowed to stand at 5° C. for 20 h and then poured into 250 ml of ice water with vigorous stirring. The product was filtered, washed with water and dried to give almost pure 4,5-epoxy-6-methylenandrosta-3,17-dione (α/β-mixture) in about 89% yield.

$C_{20}H_{26}O_3$ calcd: C 76.40 H 8.34 found: C 76.35 H 8.25 MS (m/z) 314 IR $cm^{-1}$ (KBr): 3020 (=$CH_2$), 1740 (17-keto), 1715 (3-keto), 1260 (epoxy)

EXAMPLE 9

4-azido-6-methylenandrosta-1,4-diene-3,17-dione

To a vigorously stirred mixture of 6-methylenandrosta-1,4-diene-3,17-dione (2.964 g, 10 mmol) in anhydrous ether (100 ml) cooled to −5° C. was added dropwise in about 20 min a 1M bromine solution in acetic acid (10 ml, 10 mmol).

13

The bromination was terminated after ½ h further stirring at −5° C. (TLC monitoring). Then ethanol was added, the solution concentrated under vacuum and the product precipitated by addition of water. The precipitate was submitted to flash chromatography on silica gel (hexane/ethyl acetate 7:3) to give almost pure 6β-bromo-6α-bromomethylandrosta-1,4-diene-3,17-dione in 57% yield (2.6 g).

To a solution of 6β-bromo-6α-bromomethylandrosta-1,4-diene- 3,17-dione (2.600 g, 5.7 mmol) in dimethylformamide (50 ml) was added lithium carbonate (0.422 g, 5.7 mmol).

Then a solution of sodium azide (0.371 g, 5.7 mmol) in water (6 ml) was added dropwise in about ¼ h.

The reaction mixture was stirred for further 2 h. During this operation the temperature raised to about 35° C. and then fell to room temperature. Finally water was added to precipitate almost pure 4-azido-6-methylenandrosta-1, 4-diene- 3,17-dione. Yield about 83% (1.59 g).

$C_{20}H_{23}N_3O_2$ calcd: C 71.19 H 6.87 N 12.45 Found: C 71.05 H 6.75 N 12.35 MS (m/z) 337

EXAMPLE 10

4-acetamino-6-bromo-6-bromomethylandrosta-1,4-diene-3,17-dione

To a stirred solution of 4-azido-6-methylenandrosta-1,4-diene- 3,17-dione (3.374 g, 10 mmol) in tetrahydrofuran (25 ml) was added portionwise triphenylphosphine (2.823 g, 10 mmol). During the reaction, which lasted about 2.5 h, the temperature raised to about 35° C. and there was nitrogen evolution. Then dioxane (100 ml) and water (10 ml) was added and the mixture was refluxed for 10 h. Finally the mixture was poured onto water and the raw product extracted with ethyl acetate. The organic phase was extracted 4× with 2N hydrochloric acid, the aqueous phase was separated and the product precipitated by alkalinization with sodium hydroxide solution. Thus almost pure 4-amino-6-methylen-androsta-1,4-diene-3,17dione was obtained in about 30% yield (0.934 g).

To a cooled solution of 4-amino-β-methylenandrosta-1, 4-diene- 3,17-dione (0.934, 3 mmol) in dry pyridine (2 ml) was added acetic anhydride (1.224 g, 12 mmol) and the mixture maintained at 0°–5 C. overnight.

The solvent was removed in vacuum, the residue dissolved in dichloromethane, the organic layer washed with water and then evaporated under reduced pressure. The crude product was crystallized from benzene to yield almost pure 4-acetamino-6-methylenandrosta-1,4-diene-3,17-dione in about 80% yield (0.847 g).

To a stirred mixture of 4-acetamino-6-methylenandrosta-1,4-diene-3,17-dione (0.847 g, 2.4 mmol) in anhydrous ether (25 ml) cooled to about −5° C. was added dropwise in about 15 min 1M bromine solution in acetic acid (2.4 ml, 2.4 mmol). The mixture was stirred for further ½ h at −5° C. Then ethanol was added, the solution concentrated under vacuum and the product precipitated by addition of water. The precipitate was submitted to flash chromatography on silica gel with hexane/ethyl acetate 7:3 to give almost pure 4-acetamino-6-bromo-6-bromomethylandrosta- 1,4-diene-3,17-dione in about 50% yield.

$C_{22}H_{27}Br_2NO_3$ calcd: C 51.48 H 5.30 Br 31.14 N 2.73 found: C 51.35 H 5.21 Br 30.90 N 2.65 MS m/z 513

14

EXAMPLE 11

Tablets each weighing 0.150 g and containing 25 mg of the active substance, were manufactured as follows:

| Composition (for 10,000 tablets): | |
|---|---|
| 3,17-dioxo-1'H-androst-4-eno[4,5-b] pyrrole | 250 g |
| Lactose | 800 g |
| Corn starch | 415 g |
| Talc powder | 30 g |
| Magnesium stearate | 5 g |

The 3,17-dioxo-1'H-androst-4-eno[4,5-b]pyrrole, the lactose and half the corn starch were mixed; the mixture was then forced through a sieve of 0.5 mm mesh size. Corn starch (10 g) was suspended in warm water (90 ml) and the resulting paste was used to granulate the powder.

The granulate was dried, comminuted on a sieve of 1.4 mm mesh size, then the remaining quantity of starch, talc and magnesium stearate was added, carefully mixed and processed into tablets.

EXAMPLE 12

Capsules, each dosed at 0.200 g and containing 20 mg of the active substance were prepared.

| Composition for 500 capsules: | |
|---|---|
| 3,17-dioxo-1'H-androsta-1,4-dieno[4,5-b] pyrrole | 10 g |
| Lactose | 80 g |
| Corn starch | 5 g |
| Magnesium stearate | 5 g |

This formulation was encapsulated in two-piece hard gelating capsules and dosed at 0.200 g for each capsule.

We claim:

1. A compound of formula (I)

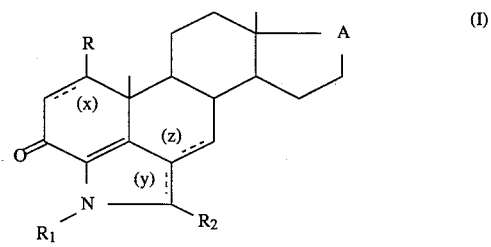

wherein x, y, z represent single or double bonds;

R is hydrogen or $C_1$–$C_4$ alkyl;

$R_1$ is hydrogen or an acyl group;

$R_2$ is hydrogen; $C_1$–$C_4$ alkyl unsubstituted or substituted by phenyl; phenyl unsubstituted or substituted by $C_1$–$C_4$ alkyl or $C_1$–$C_4$ alkoxy;

A is a >C=O, >C〰OH or >C〰$OR_3$ group, in which $R_3$ is an acyl group, provided that one of y and z is a double bond and the other is a single bond.

2. A compound of formula (I), according to claim 1 wherein

A is a >C=O, >C〰OH or >C〰$OR_3$ group;

R, $R_1$ and $R_2$ are hydrogen;

x, y, z represent single or double bonds, provided that one of y and z is a double bond and the other is a single bond.

3. A compound selected from the group consisting of
3,17-dioxo-1'H-androst-4-eno[4,5-b]pyrrole;
17β-hydroxy-3-oxo-1'H-androst-4-eno[4,5-b]pyrrole;
17β-acetoxy-3-oxo-1'H-androst-4-eno[4,5-b]pyrrole;
3,17-dioxo-1'H-androsta-1,4-dieno[4,5-b]pyrrole;
17β-hydroxy-3-oxo-1'H-androsta-1,4-dieno[4,5-b]pyrrole
17β-acetoxy-3-oxo-1'H-androsta-1,4-dieno[4,5-b]pyrrole
3,17-dioxo-1'H-androsta-4,6-dieno[4,5-b]pyrroline;
17β-hydroxy-3-oxo-1'H-androsta-4,6-dieno[4,5-b]pyrroline;
17β-acetoxy-3-oxo-1'H-androsta-4,6-dieno[4,5-b]pyrroline;
3,17-dioxo-1'H-androsta-1,4,6-trieno[4,5-b]pyrroline;
17β-hydroxy-3-oxo-1'H-androsta-1,4,6-trieno[4,5-b]pyrroline; and
17β-acetoxy-3-oxo-1'H-androsta-1,4,6-trieno [4,5-b]pyrroline.

4. A pharmaceutical composition, comprising:
(a) a pharmaceutically acceptable carrier and/or diluent; and
(b) a compound of formula (I)

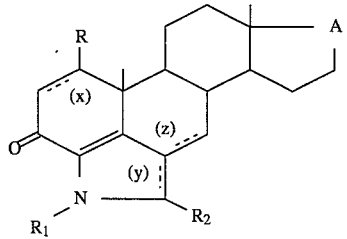

wherein
x, y, z represent single or double bonds;
R is hydrogen or $C_1$–$C_4$ alkyl;
$R_1$ is hydrogen or an acyl group;
$R_2$ is hydrogen; $C_1$–$C_4$ alkyl unsubstituted or substituted by phenyl; phenyl unsubstituted or substituted by $C_1$–$C_4$ alkyl or $C_1$–$C_4$ alkoxy;
A is a >C=O, >CH—OH or >CH—OR$_3$ group, in which $R_3$ is an acyl group, provided that one of y and z is a double bond and the other is a single bond.

5. The pharmaceutical composition of claim 4 wherein in said compound of formula (I)
A is a >C=O, >CH—OH, or >CH—OR$_3$ group;
R, $R_1$, and $R_2$ are hydrogen;
x, y, z represent single or double bonds, provided that one of
y and z is a double bond and the other is a single bond.

6. The pharmaceutical composition of claim 4, wherein said compound of formula (I) is selected from the group consisting of 3,17-dioxo-1'H-androst-4-eno[4,5-b]pyrrole; 17β-hydroxy- 3-oxo-1'H-androst-4-eno[4,5-b]pyrrole; 17β-acetoxy-3-oxo- 1'H-androst-4-eno[4,5-b]pyrrole; 3,17-dioxo-1'H-androsta-1,4-dieno[4,5-b]pyrrole; 17β-hydroxy-3-oxo-1'H-androsta-1,4-dieno[4,5-b]pyrrole, 17β-acetoxy-3-oxo-1'H-androsta-1,4-dieno[4,5-b]pyrrole, 3,17-dioxo-1'H-androsta-4,6-dieno[4,5-b]pyrroline; 17β-hydroxy-3-oxo-1'H-androsta-4,6-dieno[4,5-b]pyrroline; 17β-acetoxy-3-oxo-1'H-androsta-4,6-dieno[4,5-b]pyrroline; 3,17-dioxo-1'H-androsta-1,4,6-trieno[4,5-b]pyrroline; 17β-hydroxy-3-oxo-1'H-androsta-1,4,6-trieno[4,5-b]pyrroline; and 17β-acetoxy-3-oxo-1'H-androsta-1,4,6-trieno[4,5-b]pyrroline.

7. A method for inhibiting aromatase in a patient, comprising administering an aromatase inhibitory effective amount of a compound of formula (I)

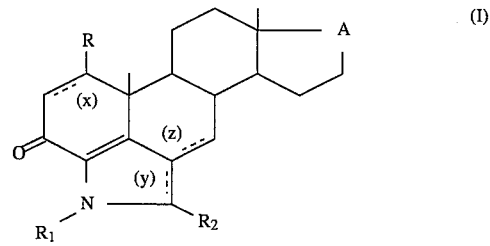

wherein
x, y, z represent single or double bonds;
R is hydrogen or $C_1$–$C_4$ alkyl;
$R_1$ is hydrogen or an acyl group;
$R_2$ is hydrogen; $C_1$–$C_4$ alkyl unsubstituted or substituted by phenyl; phenyl unsubstituted or substituted by $C_1$–$C_4$ alkyl or $C_1$–$C_4$ alkoxy;
A is a >C=O, >CH—OH or >CH—OR$_3$ group, in which $R_3$ is an acyl group, provided that one of y and z is a double bond and the other is a single bond, to a patient in need thereof.

8. The method of claim 7 wherein in said compound of formula (I)
A is a >C=O, >CH—OH, or >CH—OR$_3$ group;
R, $R_1$, and $R_2$ are hydrogen;
x, y, z represent single or double bonds, provided that one of
y and z is a double bond and the other is a single bond.

9. The method of claim 7, wherein said compound of formula (I) is selected from the group consisting of 3,17-dioxo- 1'H-androst-4-eno[4,5-b]pyrrole;
17β-hydroxy-3-oxo-1'H-androst-4-eno[4,5-b]pyrrole;
17β-acetoxy-3-oxo-1'H-androst-4-eno[4,5-b]pyrrole;
3,17-dioxo-1'H-androsta-1,4-dieno[4,5-b]pyrrole;
17β-hydroxy-3-oxo-1'H-androsta-1,4-dieno[4,5-b]pyrrole,
17β-acetoxy-3-oxo-1'H-androsta-1,4-dieno[4,5-b]pyrrole,
3,17-dioxo-1'H-androsta-4,6-dieno[4,5-b]pyrroline;
17β-hydroxy-3-oxo-1'H-androsta-4,6-dieno[4,5-b]pyrroline;
17β-acetoxy-3-oxo-1'H-androsta-4,6-dieno[4,5-b]pyrroline;
3,17-dioxo-1'H-androsta-1,4,6-trieno[4,5-b]pyrroline;
17β-hydroxy-3-oxo-1'H-androsta-1,4,6-trieno[4,5-b]pyrroline; and
17β-acetoxy-3-oxo-1'H-androsta-1,4,6-trieno[4,5-b]pyrroline.

* * * * *

UNITED STATES PATENT AND TRADEMARK OFFICE
CERTIFICATE OF CORRECTION

PATENT NO. : 5,457,097

DATED : October 10, 1995

INVENTOR(S) : Franco BUZZETTI et al

Page 1 of 3

It is certified that error appears in the above-identified patent and that said Letters Patent is hereby corrected as shown below:

On the title page, item [54] and Column 1,
"ANDROST-4-ENO[4,5-B]PYRROLE DERIVATIVES" should read
--ANDROST-4-ENO[4,5-b]PYRROLE DERIVATIVES--.

In the Abstract, 4th line from the bottom, "A is a >C═O, >C∧∧∧OH or >C∧∧∧OR₃ group" should read --A is a >C═O, >CH∧∧∧OH or >CH∧∧∧OR₃ group--.

Column 1, line 2,     "ANDROST-4-ENO[4,5-B]PYRROLE DERIVATIVES" should read --ANDROST-4-ENO[4,5-b]PYRROLE DERIVATIVES--;

line 6,     "arid to their use as" should read --and to their use as--;

line 10,     "off androgens" should read --of androgens--;

line 63,     A is a >C═O, >C∧∧∧OH or >C∧∧∧OR₃ group" should read --A is a >C═O, >CH∧∧∧OH or >CH∧∧∧OR₃ group--.

UNITED STATES PATENT AND TRADEMARK OFFICE
CERTIFICATE OF CORRECTION

PATENT NO. : 5,457,097

DATED : October 10, 1995

INVENTOR(S) : Franco BUZZETTI et al

It is certified that error appears in the above-identified patent and that said Letters Patent is hereby corrected as shown below:

Column 2, line 10, "A is C∿∿∿OH or >C∿∿∿OR$_3$" should read --A is >CH∿∿∿OH or >CH∿∿∿OR$_3$--;

line 46, "A is a >C=O,>C∿∿∿OH or >C∿∿∿OA$_c$ group" should read --A is a >C=O,>CH∿∿∿OH or >CH∿∿∿OA$_c$ group--.

Column 4, line 47, "A is a >C∿∿∿OR$_3$" should read --A is a >CH∿∿∿OR$_3$--.

Column 6, line 19, "A is C∿∿∿OH" should read --A is CH∿∿∿OH;

line 21, "is >C∿∿∿OR$_3$ group" should read --is >CH∿∿∿OR$_3$ group--;

line 24, "group and is" should read --group and R$_1$ is;

line 67, "C∿∿∿OR$_3$ group" should read --CH∿∿∿OR$_3$ group.

Column 10, line 29, "elegant" should read --eluant--.

Column 11, line 20, "$C_{20}H_{29}NO_3$" should read --$C_{22}H_{29}NO_3$--.

UNITED STATES PATENT AND TRADEMARK OFFICE
CERTIFICATE OF CORRECTION

PATENT NO. : 5,457,097

DATED : October 10, 1995

INVENTOR(S) : Franco BUZZETTI et al

It is certified that error appears in the above-identified patent and that said Letters Patent is hereby corrected as shown below:

Column 14, line 61, "A is a >C═O, >C∧∧∧/OH or >C∧∧∧/OR₃ group" should read --A is a >C═O, >CH∧∧∧/OH or >CH∧∧∧/OR₃ group--;

line 66, "A is a >C═O, >C∧∧∧/OH or >C∧∧∧/OR₃ group" should read --A is a >C═O, >CH∧∧∧/OH or >CH∧∧∧/OR₃ group--.

Signed and Sealed this

Twenty-third Day of July, 1996

BRUCE LEHMAN

*Attest:*

*Attesting Officer*    *Commissioner of Patents and Trademarks*